United States Patent

Gayer et al.

Patent Number: 4,841,086
Date of Patent: Jun. 20, 1989

[54] PROCESS FOR THE PREPARATION OF 2-CYANO-2-OXIMINO-ACETAMIDE DERIVATIVES

[75] Inventors: Herbert Gayer, Monheim; Klaus Jelich, Wuppertal, both of Fed. Rep. of Germany

[73] Assignee: Bayer Aktiengesellschaft, Leverkusen, Fed. Rep. of Germany

[21] Appl. No.: 146,051

[22] Filed: Jan. 20, 1988

[30] Foreign Application Priority Data

Jan. 27, 1987 [DE] Fed. Rep. of Germany ....... 3702283

[51] Int. Cl.$^4$ .................. C07C 121/66; C07C 121/84; C07D 295/16
[52] U.S. Cl. .................................... 558/301; 544/159; 544/163; 544/406; 546/245; 548/262; 548/378; 548/540
[58] Field of Search .......................................... 558/301

[56] References Cited

FOREIGN PATENT DOCUMENTS 231295 6/1973 Fed. Rep. of Germany .

OTHER PUBLICATIONS

Zabicky, "The Chemistry of Amides", (1970), pp. Intersciences Publishers, London-N.Y.-Sydney-Toronto.
Weygand/Hilgetag, "Preparative Organic Chemistry", (1972), p. 499; John Wiley & Sons, N.Y.-London-Sydney-Toronto.
Sidgwick, "The Organic Chemistry of Nitrogen", 3rd ed., (1966), p. 228; Clarendon Press, Oxford.
Chem. Ber.; 54, p. 1342, (1921).
Fritz Baum; "Zur Kenntnis der Traubeschen Pyrimidin-synthese". Chem. Berichte 41 (1908), pp. 532-540.
Döpp et al., "Carbonsäure-amide . . .", Houben Weyl, E V, p. 1000.
Synthesis (1979), pp. 527-529 and 549-552.
Synthesis (1981) (pp. 1005-1008).
Chem. Berichte (1909), "Isonitroso-cyanacetamid . . .", pp. 738-739.

Primary Examiner—Joseph P. Brust
Attorney, Agent, or Firm—Sprung Horn Kramer & Woods

[57] ABSTRACT

A process for the preparation of a 2-cyano-2-oximino-acetamide derivative of the formula

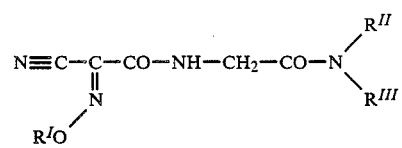

in which
$R^I$ is alkyl or other organic radical,
$R^{II}$ is hydrogen or alkyl,
$R^{III}$ is hydrogen, alkyl or other organic radical which comprises reacting a 2-cyano-2-oximino-acetamide of the formula

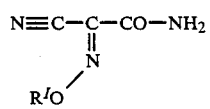

with a base B at a temperature between 0° C. and 100° C., to produce a salt of the formula

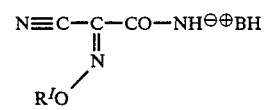

in which
B represents one equivalent of an organic of inorganic base,
and reacting such salt with an alkylating agent of the formula

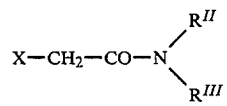

in which
X is halogen, methane- or p-toluenesulphonate or methyl sulphate, at a temperature between 0° C. and 150° C.

2 Claims, No Drawings

PROCESS FOR THE PREPARATION OF 2-CYANO-2-OXIMINO-ACETAMIDE DERIVATIVES

The present invention relates to a new process for the preparation of known 2-cyano-2-oximino-acetamide derivatives which have fungicidal properties.

It has already been disclosed that 2-cyano-2-oximino-acetamide derivatives can be prepared by, for example, (a) reacting acid chlorides with amines in the presence of an inert organic solvent, such as, for example, ether or toluene, and in the presence of an organic or inorganic acid-binding agent, such as, for example, triethylamine or sodium carbonate, at temperatures between 0° and 120° C. according to the following reaction equation:

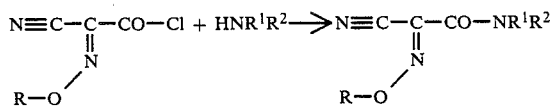

where the radicals denote, for example:
R=alkyl, alkenyl, alkinyl or optionally substituted phenylalkyl,
$R^1$=H or alkyl and
$R^2$=optionally substituted alkyl with a broad variation of substituents, or (b) reacting esters with amines in the presence of an inert organic solvent, such as, for example, alcohols or dimethylformamide, at temperatures between 0° and 150° C. according to the following reaction equation:

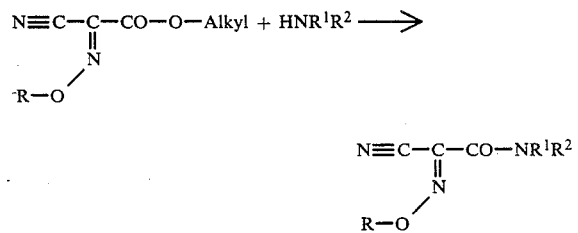

where the radicals denote, for example:
R=alkyl, alkenyl, alkinyl or optionally substituted phenylalkyl,
$R^1$=H or alkyl and
$R^2$=optionally substituted alkyl with a broad variation of substituents, or (c) reacting oximes initially with a base, such as, for example, sodium ethylate, in the presence of an inert organic solvent, such as, for example, ethanol or acetonitrile, at temperatures between 0° and 150° C., and alkylating the resultant salt in a conventional fashion, according to the following reaction equation:

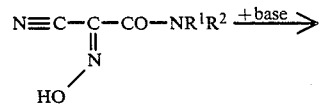

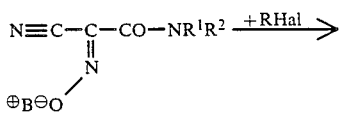

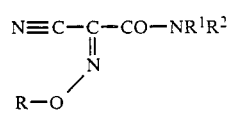

where the radicls denote, for example:
R=alkyl, alkenyl, alkinyl, or optionally substituted phenylalkyl,
$R^1$=H or alkyl,
$R^2$=an optionally substituted alkyl with a broad variation of substituents, and
Hal=halogen, or (d) reacting acetamide derivatives initially with a strong base, such as, for example, sodium hydride, in the presence of an inert organic solvent, such as, for example, dimethylformamide, at temperatures between −30° and +100° C.; and subsequently alkylating in a conventional fashion, if appropriate with isolation of the resultant salt, and according to the following reaction equation:

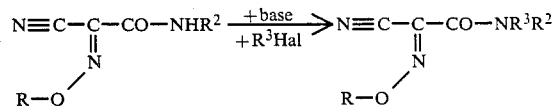

where the radicals denote, for example:
R=alkyl, alkenyl, alkinyl, or optionally substituted phenylalkyl,
$R^3$=cyanoalkyl, alkenyl, alkinyl,
$R^2$=optionally substituted alkyl with a broad variation of the substituents, and
Hal=halogen (in this respect, cf., for example, the information according to DE-OS (German Published Specification) No. 2,312,956, EP No. 0,201,999 and U.S. Ser. No. 868,844 filed May 29, 1986, now pending).

However, these process variants exhibit a number of disadvantages. Thus, the acid chlorides which are required for process (a) are problematic with respect to their handling since there is a danger of explosion. The esters which are required for process (b) can be obtained in pure form only with great difficulty, particularly on a relatively large scale. Purification problems also occur in process (c), here in the isolation of the final products. Process (d) gives only disubstituted amides corresponding to the description. In this process, the handling of the bases sodium hydride and lithium diisopropylamide which are preferably used for protonation of the acetamide derivatives where $R^2$=alkyl is not without danger.

It has been found that the known 2-cyano-2-oximino-acetamide derivatives of the formula (I)

$$N≡C-\underset{\underset{R^IO}{\overset{\|}{N}}}{C}-CO-NH-CH_2-CO-N\underset{R^{III}}{\overset{R^{II}}{\diagdown}} \quad (I)$$

in which
- $R^I$ represents alkyl, alkenyl, alkinyl, cyanoalkyl, azolylalkyl, optionally substituted phenylalkyl or optionally substituted cycloalkyl,
- $R^{II}$ represents hydrogen or alkyl,
- $R^{III}$ represents hydrogen, alkyl, alkenyl, alkinyl, halogenoalkyl, alkoxyalkyl, dialkylaminoalkyl, alkoxycarbonylalkyl, hydroxycarbonylalkyl, aminocarbonylalkyl, alkylaminocarbonylalkyl, dialkylaminocarbonylalkyl, cyanoalkyl, optionally substituted phenylalkyl, optionally substituted phenyl, optionally substituted cycloalkyl, an acylamino radical or the $$-N=CH-R^{IV}$$

group, where
- $R^{IV}$ represents alkyl or optionally substituted phenyl,
- $R^{II}$ and $R^{III}$, together with the nitrogen atom to which they are bound, represent an optionally substituted heterocyclic ring which may contain further hetero atoms, are obtained when 2-cyano-2-oximino-acetamides of the formula (II)

$$N≡C-\underset{\underset{R^IO}{\overset{\|}{N}}}{C}-CO-NH_2 \quad (II)$$

in which
$R^I$ has the abovementioned meaning, are reacted with a base B, if appropriate in the presence of a diluent, at temperatures between 0° C. and 100° C., and the resultant salts of the formula (III)

$$N≡C-\underset{\underset{R^IO}{\overset{\|}{N}}}{C}-CO-NH^{\ominus\oplus}BH \quad (III)$$

in which
- $R^I$ has the abovementioned meaning, and
- B represents one equivalent of an organic or inorganic base, are reacted directly or, if appropriate, after intermediate isolation, with an alkylating agent of the formula (IV)

$$X-CH_2-CO-N\underset{R^{III}}{\overset{R^{II}}{\diagdown}} \quad (IV)$$

in which
- $R^{II}$ and $R^{III}$ have the abovementioned meaning, and
- X represents halogen, methane- or p-toluenesulphonate or methyl sulphate, if appropriate in the presence of a diluent, at temperatures between 0° C. and 150° C.

It is surprising that the process according to the invention is so broadly applicable. A self-condensation of the molecule part $$NC-C\underset{NOR^I}{\overset{\diagup}{\diagdown\!\!\!\diagdown}}$$

of the 2-cyano-2-oximino-acetamides of the formula (II) with the carbamoyl part $-CO-NH_2$ of the acetamide of the formula (II) or with the corresponding part of $-CO-NH^{\ominus}BH^{\oplus}$ of the salts of the formula (III) was entirely to be expected. In addition, double alkylation of the acetamides of the formula (II) was also expected.

The process according to the invention has the advantage that the starting materials of the formula (II) are compounds which are easily accessible and simple to prepare in pure form (cf., for example, Chem. Ber. 54, 1342 (1921)).

The final products of the formula (I) and the precursors of the formula (II) can exist in the geometrical isomers E and Z or as mixtures of isomers.

Formula (I) provides a general definition of the 2-cyano-2-oximino-acetamide derivatives which can be obtained by the process according to the invention. Preferred compounds of the formula (I) are those in which $R^I$ represents straight-chain or branched alkyl having 1 to 8 carbon atoms, alkenyl or alkinyl in each case having 2 to 4 carbon atoms in the alkyl part, cyanoalkyl having 1 to 4 carbon atoms, 1,2,4-triazol-1-ylalkyl and pyrazol-1-ylalkyl in each case having 1 to 6 carbon atoms in the alkyl part, phenylalkyl, having 1 to 4 carbon atoms in the alkyl part, which is optionally monosubstituted, disubstituted or trisubstituted in the phenyl part by identical or different substituents, substituents which may preferably be mentioned being: halogen, cyano, nitro, hydroxyl, alkyl, alkoxy, alkylthio, alkylsulphinyl and alkylsulphonyl in each case having 1 to 4 carbon atoms, and phenyl which is optionally monosubstituted, disubstituted or trisubstituted by halogen, the substituents being identical or different; or represents cycloalkyl having 3 to 7 carbon atoms which is optionally monosubstituted, disubstituted or trisubstituted by identical or different substituents, substituents which may preferably be mentioned being halogen and alkyl having 1 to 4 carbon atoms; $R^{II}$ represents hydrogen or straight-chain or branched alkyl having 1 to 4 carbon atoms; $R^{III}$ represents hydrogen, straight-chain or branched alkyl having 1 to 4 carbon atoms, alkenyl or alkinyl in each case having 2 to 4 carbon atoms, halogenoalkyl having 1 to 4 carbon atoms and 1 to 5 identical or different halogen atoms, alkoxyalkyl having 1 to 4 carbon atoms in each of the alkoxy part and the alkyl part, dialkylaminoalkyl having up to 4 carbon atoms in the individual alkyl parts, alkoxycarbonylalkyl having 1 to 4 carbon atoms in each of the alkoxy part and the alkyl part, hydroxycarbonylalkyl having 1 to 4 carbon atoms in the alkyl part, aminocarbonylalkyl, alkylaminocarbonylalkyl or dialkylaminocarbonylalkyl in each case having 1 to 4 carbon atoms in each alkyl part, cyanoalkyl having 1 to 4 carbon atoms in the alkyl part, phenylalkyl, having 1 to 4 carbon atoms in the alkyl part, which is optionally monosubstituted, disubstituted or trisubstituted in the phenyl part by identical or different substituents, or phenyl which is optionally monosubstituted, disubstituted or trisubstituted by identical or different substituents, suitable substituents in each case being the phenyl substituents which have already been mentioned in the case of $R^I$, represents cycloalkyl having 3 to 7 carbon atoms which is optionally substituted by identical or different substituents, suitable substituents preferably being halogen and alkyl having 1 to 4 carbon atoms, represents alkylcarbonylamino or alkoxycarbonylamino in each case having 1 to 4 carbon atoms in the alkyl part and in the alkoxy part respectively, in addition represents aminocarbonylamino, alkylaminocarbonylamino or dialkylaminocarbonylamino in each case having 1 to 4 carbon atoms in the individual alkyl parts, or represents formylamino or the $-N=CH-R^{IV}$ group, where $R^{IV}$ represents straight-chain or branched alkyl having 1 to 4 carbon atoms or phenyl which is optionally monosubstituted, disubstituted or trisubstituted by identical or different substituents, suitable substituents being the phenyl substituents which have already been mentioned in the case of $R^I$, $R^{II}$ and $R^{III}$, together with the nitrogen atom to which they are bound, represent a 5- or 6-membered heterocyclic ring which may, if appropriate, contain oxygen or nitrogen as further hetero atoms and may optionally be substituted by cyano, halogen, alkyl having 1 to 4 carbon atoms, hydroxycarbonyl, alkoxycarbonyl having 1 to 4 carbon atoms in the alkoxy part, amino carbonyl, and alkylaminocarbonyl and dialkylaminocarbonyl in each case having 1 to 4 carbon atoms in the individual alkyl parts; and X represents chlorine, bromine, iodine, methanesulphonate, p-toluenesulphonate or methyl sulphate. Particularly preferred compounds of the formula (I) are those in which $R^I$ represents straight-chain or branched alkyl having 1 to 4 carbon atoms, allyl, propargyl, cyanomethyl, cyanoethyl, 1,2,4-triazol-1-ylalkyl and pyrazol-1-ylalkyl in each case having 1 to 4 carbon atoms in the alkyl part, phenylalkyl, having 1 or 2 carbon atoms in the alkyl part, which is optionally monosubstituted or disubstituted in the phenyl part by identical or different substituents, substituents which may be mentioned in particular being: fluorine, chlorine, cyano, nitro, hydroxyl, methyl, methoxy, methylthio, methylsuphinyl, methylsulphonyl and phenyl which is optionally monosubstituted or disubstituted by fluorine or chlorine, the substituents being identical or different; furthermore represents cyclopropyl, cyclobutyl, cyclopentyl, cyclohexyl or cycloheptyl which is in each case optionally monosubstituted or disubstituted by fluorine, chlorine or methyl, the substituents being identical or different;

$R^{II}$ represent hydrogen, methyl or ethyl;

$R^{III}$ represents hydrogen, methyl, ethyl, n-propyl, i-propyl, n-butyl, i-butyl, sec.-butyl, tert.-butyl, allyl, propargyl, halogenoalkyl having 1 or 2 carbon atoms and 1 to 3 identical or different halogen atoms, such as fluorine and chlorine atoms, alkoxyalkyl having 1 or 2 carbon atoms in each of the alkoxy part and the alkyl part, dialkylaminoalkyl having 1 or 2 carbon atoms in the individual alkyl parts, alkoxycarbonylalkyl, hydroxycarbonylalkyl, aminocarbonylalkyl, alkylaminocarbonylalkyl with dialkylaminocarbonylalkyl in each case having 1 or 2 carbon atoms in each alkyl part, cyanoalkyl having 1 to 4 carbon atoms in the alkyl part; furthermore represents phenylalkyl, having 1 or 2 carbon atoms in the alkyl part, which is optionally monosubstituted or disubstituted in the phenyl part by identical or different substituents, represents phenyl which is monosubstituted or disubstituted by identical or different substituents, suitable substituents in each case being the phenyl substituents which have already been mentioned in the case of $R^I$; represents cyclopropyl, cyclobutyl, cyclopentyl, cyclohexyl or cycloheptyl which is in each case optionally monosubstituted or disubstituted by fluorine, chlorine or methyl, the substituents being identical or different, alkylcarbonylamino or alkoxycarbonylamino in each case having 1 or 2 carbon atoms in the alkyl part and in the alkoxy part respectively, aminocarbonylamino, methylaminocarbonylamino, ethylaminocarbonylamino, dimethylaminocarbonylamino, diethylaminocarbonylamino, methylethylaminocarbonylamino, or formylamino or the $-N=CH-R^{IV}$ group, where $R^{IV}$ represents methyl, ethyl, or phenyl which is optionally monosubstituted or disubstituted by identical or different substituents, suitable substituents being the phenyl substituents which have already preferably been mentioned in the case of $R^I$; or $R^{II}$ and $R^{III}$, together with the nitrogen atom to which they are bound, represent a 5- or 6-membered heterocyclic ring which may contain, if appropriate, oxygen or nitrogen as further hetero atoms, such as, in particular, piperidine, pyrollidine, morpholine or piperazine, and which may optionally be substituted by cyano, fluorine, chlorine, bromine, iodine, methyl, ethyl, i-propyl, hydroxycarbonyl, methoxycarbonyl, ethoxycarbonyl, aminocarbonyl, methylaminocarbonyl, ethylaminocarbonyl, dimethylaminocarbonyl, diethylaminocarbonyl and methyethylaminocarbonyl; and X represents chlorine or bromine.

If, for example, 2-cyano-2-methoximino-acetamide is used as starting material, potassium tert.-butylate is used as base and N,N-diethylchloroacetamide is used as alkylating agent, the course of the process according to the invention may be illustrated by the following equation:

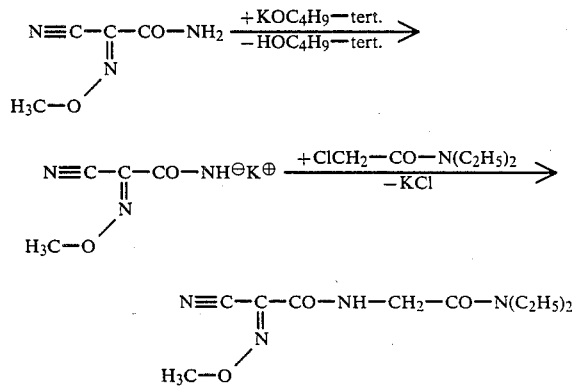

Formula (II) provides a general definition of the 2-cyano-2-oximino-acetamides to be used as starting material in the process according to the invention. Preferred compounds of the formula (II) are those in which $R^I$ represents a straight-chain or branched alkyl having 1 to 8 carbon atoms, alkenyl or alkinyl in each case having 2 to 4 carbon atoms in the alkyl part, cyanoalkyl having 1 to 4 carbon atoms, 1,2,4-triazol-1-ylalkyl and pyrazol-1-ylalkyl in each case having 1 to 6 carbon atoms in the alkyl part, phenylalkyl, having 1 to 4 carbon atoms in the alkyl part, which is optionally monosubstituted, disubstituted or trisubstituted in the phenyl part by identical or different substituents, substituents which may preferably be mentioned being: halogen, cyano, nitro, hydroxyl, alkyl, alkoxy, alkylthio, alkylsulphinyl and alkylsulphonyl in each case having 1 to 4 carbon atoms, and phenyl which is optionally monosubstituted, disubstituted or trisubstituted by identical or different halogen; or represents cycloalkyl having 3 to 7 carbon atoms which is optionally monosubstituted, disubstituted or trisubstituted by identical or different substituents, substituents which may probably be mentioned being halogen and alkyl having 1 to 4 carbon atoms. Particularly preferred starting materials are those compounds of the formula (II) in which $R^I$ represents straight-chain or branched alkyl having 1 to 4 carbon atoms, allyl, propargyl, cyanomethyl, cyanoethyl, 1,2,4-triazol-1-ylalkyl and pyrazol-1-ylalkyl in each case having 1 to 4 carbon atoms in the alkyl parts, phenylalkyl, having 1 to 2 carbon atoms in the alkyl part, which is optionally monosubstituted or disubstituted in the phenyl part by identical or different substituents, substituents which may be mentioned in particular being: fluorine, chlorine, cyano, nitro, hydroxyl, methyl, methoxy, methylthio, methylsulphinyl, methylsulphonyl and phenyl which is optionally monosubstituted or disubstituted by fluorine or chlorine, the substituents being identical or different; furthermore represents cyclopropyl, cyclobutyl, cyclopentyl, cyclohexyl or cycloheptyl which is in each case optionally monosubstituted or disubstituted by fluorine, chlorine or methyl, the substituents being identical or different.

The 2-cyano-2-oximino-acetamides of the formula (II) are known (cf. for example, Chem. Ber. 54, 1342, (1921)) or they can be obtained in a generally known fashion, for example by reacting alkali metal salts of 2-cyano-2-oximino-acetamides of the formula (IIa)

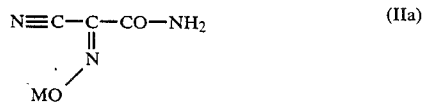

in which

M represents an alkali metal, in particular sodium, with an alkylating agent, such as, for example, dimethyl sulphate, in the presence of an inert, organic solvent, such as, for example, acetone, at temperatures between 0° C. and 60° C.

The alkali metal salts (cf. also Chem. Ber. 42, 738 (1909)) are obtained particularly advantageously by reacting cyanoacetamide with an alkyl nitrite, such as, for example, isoamyl nitrite, and an alkali metal alcoholate, such as, for example, sodium ethylate, in the presence of an alcohol, such as, for example, ethanol, at temperatures between 0° C. and 20° C.

The letter B provides a general definition of the bases additionally to be used as starting materials for the process according to the invention. B preferably represents conventional inorganic and organic bases, such as, in particular, alkali metal alcoholates, such as, for example, potassium tert.-butylate; alkali metal hydroxides and carbonates, such as, for example sodium hydroxide, potassium hydroxide and potassium carbonate: and also tetraalkylammonium or benzyltrialkylammonium hydroxides and alcoholates, such as, for example, tetramethylammonium hydroxide and alcoholate, tetrabutylammonium hydroxide and alcoholate or benzyltriethylammonium hydroxide and alcoholate.

The bases B are generally known compounds of organic chemistry.

Formula (IV) provides a general definition of the alkylating agents furthermore to be used as starting materials for the process according to the invention. Preferred compounds of the formula (IV) are those in which $R^{II}$ represents hydrogen or straight-chain or branched alkyl having 1 to 4 carbon atoms;

$R^{III}$ represents hydrogen, straight-chain or branched alkyl having 1 to 4 carbon atoms, alkenyl or alkinyl in each case having 2 to 4 carbon atoms, halogenoalkyl having 1 to 4 carbon atoms and 1 to 5 identical or different halogen atoms, alkoxyalkyl having 1 to 4 carbon atoms in each of the alkoxy part and the alkyl part, dialkylaminoalkyl having 1 to 4 carbon atoms in the individual alkyl parts, alkoxycarbonylalkyl having 1 to 4 carbon atoms in each of the alkoxy part and the alkyl part, hydroxycarbonylalkyl having 1 to 4 carbon atoms in the alkyl part, aminocarbonylalkyl, alkylaminocarbonylalkyl or dialkylaminocarbonylalkyl in each case having 1 to 4 carbon atoms in each alkyl part, cyanoalkyl having 1 to 4 carbon atoms in the alkyl part, phenylalkyl, having 1 to 4 carbon atoms in the alkyl part, which is optionally monosubstituted, disubstituted or trisubstituted, in the phenyl part by identical or different substituents or phenyl which is monosubstituted, disubstituted ir trisubstituted by identical or different substituents, suitable substituents in each case being the phenyl substituents which have already been mentioned in the case of $R^I$, represents cycloalkyl having 3 to 7 carbon atoms which is optionally substituted by identical or different substituents, suitable substituents preferably being halogen and alkyl having 1 to 4 carbon atoms, represents alkylcarbonylamino or alkoxycarbonylamino in each case having 1 to 4 carbon atoms in the alkyl part and in the alkoxy part respectively, in addition represents aminocarbonylamino, alkylaminocarbonylamino and dialkylaminocarbonylamino in each case having 1 to 4 carbon atoms in the individual alkyl parts, and formylamino or the —N=CH—$R^{IV}$ group, where $R^{IV}$ represents straight-chain or branched alkyl having 1 to 4 carbon atoms, or phenyl which is optionally monosubstituted, disubstituted or trisubstituted by identical or different substituents, suitable substituents being the phenyl substituents which have already been mentioned in the case of $R^I$, $R^{II}$ and $R^{III}$, together with the nitrogen atom to which they are bound, represent a 5- or 6-membered heterocyclic ring which may, if appropriate, contain oxygen or nitrogen as further hetero atoms and which may optionally be substituted by cyano, halogen, alkyl having 1 to 4 carbon atoms, hydroxycarbonyl, alkoxycarbonyl having 1 to 4 carbon atoms in the alkoxy part, aminocarbonyl, and alkylaminocarbonyl and dialkylaminocarbonyl in each case having 1 to 4 carbon atoms in the individual alkyl parts; and X represents chlorine, bromine, iodine, methanesulphonate, p-toluenesulphonate or methyl sulphate.

Particularly preferred starting materials are those compounds of the formula (IV) in which $R^{II}$ represents hydrogen, methyl or ethyl;

$R^{III}$ represents hydrogen, methyl, ethyl, n-propyl, i-propyl, n-butyl, i-butyl.sec.-butyl, tert.-butyl, allyl, propargyl, halogenoalkyl having 1 or 2 carbon atoms and 1 to 3 identical or different halogen atoms, such as fluorine and chlorine atoms, alkoxyalkyl having 1 or 2 carbon atoms in each of the alkoxy part and the alkyl part, dialkylaminoalkyl having 1 or 2 carbon atoms in the individual alkyl parts, alkoxycarbonylalkyl, hydroxycarbonylalkyl, aminocarbonylalkyl, alkylaminocarbonylalkyl or dialkylaminocarbonylalkyl in each case having 1 or 2 carbon atoms in each alkyl part, cyanoalkyl having 1 to 4 carbon atoms in the alkyl part; furthermore represents phenylalkyl, having 1 or 2 carbon atoms in the alkyl part, which is optionally mono-substituted or disubstituted in the phenyl part by identical or different substituents, or phenyl which is monosubstituted or disubstituted by identical or different substituents, suitable substituents in each case being the phenyl substituents which have already been mentioned in the case of $R^I$; represents cyclopropyl, cyclobutyl, cyclopentyl, cyclohexyl or cycloheptyl, which is in each case optionally monosubstituted or disubstituted by fluorine, chlorine or methyl, the substituents being identical or different, alkylcarbonylamino or alkoxycarbonylamino in each case having 1 or 2 carbon atoms in the alkyl part and in the alkoxy part respectively, aminocarbonylamino, methylaminocarbonylamino, ethylaminocarbonylamino, dimethylaminocarbonylamino, diethylaminocarbonylamino, methylethylaminocarbonylamino and formylamino, or the $-N=CH-R^{IV}$ group, where $R^{IV}$ represents methyl, ethyl or phenyl which is optionally monosubstituted or disubstituted by identical or different substituents, suitable substituents being the phenyl substituents which have already been preferably mentioned in the case of $R^I$; or $R^{II}$ and $R^{III}$, together with the nitrogen atom to which they are bound, represent a 5- or 6-membered heterocyclic ring which may, if appropriate, contain oxygen or nitrogen as further heteroatoms, such as, in particular, piperidine, pyrollidine, morpholine or piperazine, and which may optionally be substituted by cyano, fluorine, chlorine, bromine, iodine, methyl, ethyl, i-propyl, hydroxycarbonyl, methoxycarbonyl, ethoxycarbonyl, aminocarbonyl, methylaminocarbonyl, ethylaminocarbonyl, dimethylaminocarbonyl, diethylaminocarbonyl and methylethylaminocarbonyl; and X represents chlorine or bromine.

The alkylating agents of the formula (IV) are known or can be obtained in a fashion which is known per se.

Possible diluents when carrying out the process according to the invention are all organic solvents which are inert under the reaction conditions. Ethers, such as diethyl ether, diisopropyl ether, tetrahydrofuran or dioxane; ketones, such as acetone or methyl ethyl ketone, furthermore acetonitrile nd dimethylformamide may preferably be used.

The reaction temperatures may be varied within a relatively wide range when carrying out the process according to the invention. In the case of the salt formation, the reaction is generally carried out at temperatures between 0° C. and 100° C., preferably between 0° C. and 30° C., in the case of the subsequent alkylation, the reaction is generally carried out at temperatures between 0° C. and 150° C., preferably between 60° C. and 120° C.

When carrying out the process according to the invention, equimolar amounts are preferably employed, if appropriate an excess of up to 1 mole of alkylating agent of the formula (IV). If desired, the salts of the formula (III) can be isolated, but the process can also be carried out without isolation. In many cases, it has proven advantageous to initially convert the acetamides of the formula (II) into an alkali metal salt of the formula (II) and then to convert this into the corresponding ammonium salt with the aid of tetraalkylammonium or benzyltrialkylammonium chlorides or bromides. The final products of the formula (I) are isolated in a conventional fashion.

The 2-cyano-2-oximino-acetamide derivatives of the formula (I) which can be prepared by the process according to the invention are known (see U.S. Ser. No. 868,844, filed May 29, 1987, now pending). They are distinguished by very good fungicidal properties.

The process according to the invention is illustrated by the following examples.

EXAMPLE 1

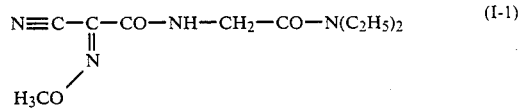

(Variant 1)

6.4 g (0.05 mol) of 2-cyano-2-methoximino-acetamide (E-isomer) are dissolved in 50 ml of tetrahydrofuran. 5.7 g (0.05 mol) of potassium tert.butylate, dissolved in 50 ml of tetrahydrofuran, are added dropwise to this solution, with cooling, at a rate such that the temperature does not exceed 20° C. The mixture is stirred for a further 15 minutes at 10° C., and the salt which crystallizes out is filtered off. 7.6 g (92% of theory=0.046 mol) of the potassium salt of 2-cyano-2-methoximinoacetamide are obtained. This product is suspended in 50 ml tetrahydrofuran. After addition of 6.9 g (0.046 mol) of N,N-diethylchloroacetamide, the mixture is refluxed for 1 hour. The mixture is subsequently concentrated and the residue is chromatographed (methylene chloride/acetone=4/1).

4.6 g (38.3% of theory) of N-(diethylcarbamoylmethyl)-2-cyano-2-methoximino-acetamide (E-isomer) of melting point 104°-06° C. are obtained.

(Variant 2)

5 ml (0.01 mol) of a 2 molar solution of sodium methylate in methanol are added to 2.3 g (0.01 mol) of benzyltriethyl ammoniumchloride in 10 ml of tetrahydrofuran, and the mixture is concentrated in vacuum at a bath temperature of below 40° C. A solution of 1.3 g (0.01 mol) of 2-cyano-2-methoximino-acetamide (E-isomer) in 20 ml of tetrahydrofuran is added to the residue at room temperature. 1.5 g (0.01 mol) of N,N-diethylchloroacetamide are added, and the mixture is refluxed for 30 minutes. After stripping off the solvent and adding 10 ml of ice water, 1.22 g (50.7% of theory) of N-(diethylcarbamoylmethyl)-2-cyano-2-methoximino-acetamide (E-isomer) of melting point 104°–06° C. crystallize out.

Preparation of the starting compound

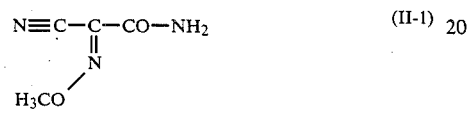

(II-1)

27 g (0.2 mol) off the sodium salt of 2-cyano-2-oximino-acetamide (E-isomer) and 25.3 g (0.2 mol) of dimethyl sulphate are refluxed for 10 minutes in 200 ml of acetone. After cooling to room temperature, 25 g of the sodium salt of O-methylsulphuric acid are filtered off. The acetone is stripped off and the residue is stirred with 100 ml of water for 30 minutes at room temperature, then for 1 hour at 0° C. The mixture is filtered, and 20.8 g (81.82% of theory) of 2-cyano-2-methoximinoacetamide (E-isomer) of melting point 168°–169° C. are obtained.

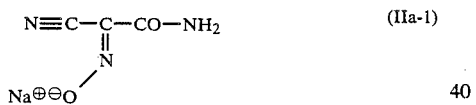

(IIa-1)

11.5 g (0.5 mol) of sodium are dissolved in 200 ml of ethanol. This solution is added dropwise at a temperature of below 20° C. to a mixture of 42 g (0.5 mol) of cyanoacetamide, 64.4 g (0.55 mol) of isoamyl nitrite and 300 ml of ethanol. The mixture is stirred for 1 hour at room temperature, and the product is then filtered off.

60.1 g (89% of theory) of the sodium salt of 2-cyano-2-oximinoacetamide (E-isomer) are obtained.

It is understood that the specification and examples are illustrative but not limitative of the present invention and that other embodiments within the spirit and scope of the invention will suggest themselves to those skilled in the art.

We claim:

1. A process for the preparation of a 2-cyano-2-oximino-acetamide derivative of the formula

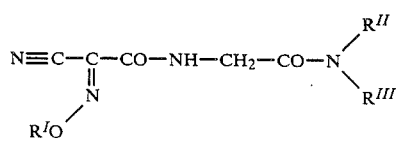

in which
$R^I$ represents straight-chain or branched alkyl having 1 to 4 carbon atoms, allyl, propargyl, cyanomethyl, cyanoethyl, phenylalkyl, having 1 or 2 carbon atoms in the alkyl part, which is optionally monosubstituted or independently disubstituted in the phenyl part by fluorine, chlorine, cyano, nitro, hydroxyl, methyl, methoxy, methylthio, methylsulphinyl, methylsulphonyl and phenyl which is optionally monosubstituted or disubstituted by fluorine or chlorine, the substituents being identical or different; or cyclopropyl, cyclobutyl, cyclopentyl, cyclohexyl or cycloheptyl which is in each case optionally monosubstituted or disubstituted by fluorine, chlorine or methyl, the substituents being identical or different;

$R^{II}$ represent hydrogen, methyl or ethyl;

$R^{III}$ represents hydrogen, methyl, ethyl, n-propyl, i-propyl, n-butyl, i-butyl, sec.-butyl, tert.-butyl, allyl, propargyl, halogenoalkyl having 1 or 2 carbon atoms and 1 to 3 identical or different halogen atoms, alkoxyalkyl having 1 or 2 carbon atoms in each of the alkoxy part and the alkyl part, dialkylaminoalkyl having 1 or 2 carbon atoms in the individual alkyl parts, alkoxycarbonylalkyl, hydroxycarbonylalkyl, aminocarbonylalkyl, alkylaminocarbonylalkyl with dialkylaminocarbonylalkyl in each case having 1 or 2 carbon atoms in each alkyl part, cyanoalkyl having 1 to 4 carbon atoms in the alkyl part; phenylalkyl, having 1 or 2 carbon atoms in the alkyl part, which is optionally monosubstituted or independently disubstituted in the phenyl part, or phenyl which is monosubstituted independently disubstituted, possible substituents in each cse being the phenyl substituents which have already been mentioned in the case of $R^I$; represents cyclopropyl, cyclobutyl, cyclopentyl, cyclohexyl or cycloheptyl which is in each case optionally monosubstituted or disubstituted by fluorine, chlorine or methyl, the substituents being identical or different, alkylcarbonylamino or alkoxycarbonylamino in each case having 1 or 2 carbon atoms in the alkyl part and in the alkoxy part respectively, aminocarbonylamino, methylaminocarbonylamino, ethylaminocarbonylamino, dimethylaminocarbonylamino, diethylaminocarbonylamino, methylethylaminocarbonylamino, or formylamino or the —N=CH—$R^{IV}$ group, where $R^{IV}$ represents methyl, ethyl, or phenyl which is optionally monosubstituted or independently disubstituted, possible substituents being the phenyl substituents which have already been mentioned in the case of $R^I$;

comprising reacting a 2-cyano-2-oximino-acetamide of the formula

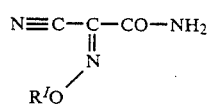

with a base B at a temperature between 0° C. and 100° C., to produce a salt of the formula

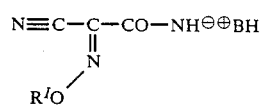

in which

B represents one equivalent of an organic of inorganic base, and reacting such salt directly or if appropriate, after intermediate isolation, with an alkylating agent of the formula

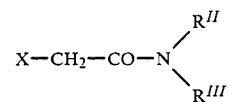

in which
X is halogen, methane- or p-toluenesulphonate or methyl sulphate, at a temperature between 0° C. and 150° C.

2. A process according to claim 1, in which the base B is an alkali metal alcoholate, alkali metal hydroxide, alkali metal carbonate, tetraalkylammonium or benzyltrialkylammonium hydroxide or alcoholate.